United States Patent
Scheibe et al.

(10) Patent No.: US 12,138,422 B2
(45) Date of Patent: Nov. 12, 2024

(54) DOSING PUMP

(71) Applicant: BÜRKERT WERKE GMBH & CO. KG, Ingelfingen (DE)

(72) Inventors: Ralf Scheibe, Ingelfingen (DE); Johannes Baumann, Ingelfingen (DE); Ralf Egner, Ingelfingen (DE); Elke Eichhorn, Ingelfingen (DE)

(73) Assignee: BÜRKERT WERKE GMBH & CO. KG, Ingelfingen (DE)

( * ) Notice: Subject to any disclaimer, the term of this patent is extended or adjusted under 35 U.S.C. 154(b) by 155 days.

(21) Appl. No.: 17/448,914

(22) Filed: Sep. 27, 2021

(65) Prior Publication Data
US 2022/0105266 A1 Apr. 7, 2022

(30) Foreign Application Priority Data
Oct. 1, 2020 (DE) ...................... 10 2020 125 757.0

(51) Int. Cl.
*A61M 5/145* (2006.01)
*A61M 5/168* (2006.01)

(52) U.S. Cl.
CPC .... *A61M 5/14593* (2013.01); *A61M 5/16881* (2013.01); *A61M 2205/0272* (2013.01)

(58) Field of Classification Search
CPC .......... A61M 5/14593; A61M 5/16881; A61M 5/14224; A61M 5/14216; A61M 2205/0272; F04B 9/02; F04B 13/00; F04B 43/02; F04B 43/04; F04B 53/144
See application file for complete search history.

(56) References Cited

U.S. PATENT DOCUMENTS

| | | | |
|---|---|---|---|
| 4,768,547 A * | 9/1988 | Danby | A61M 5/14224 137/859 |
| 5,529,467 A | 6/1996 | Rometsch | |
| 8,474,365 B2 | 7/2013 | Kaufmann et al. | |
| 10,396,646 B2 | 8/2019 | Reiter et al. | |
| 2010/0183462 A1 | 7/2010 | Kaufmann et al. | |
| 2011/0044829 A1* | 2/2011 | Stenberg | H02K 33/10 417/375 |
| 2015/0069860 A1* | 3/2015 | Reiter | F04B 43/043 251/129.01 |
| 2019/0353272 A1* | 11/2019 | Grandvallet | F16K 11/168 |

FOREIGN PATENT DOCUMENTS

| DE | 39 09 820 A1 | 9/1990 |
|---|---|---|
| DE | 44 33 068 A1 | 3/1996 |
| DE | 10 2007 028 351 A1 | 12/2008 |
| DE | 10 2013 110 029 C5 | 3/2017 |

* cited by examiner

*Primary Examiner* — Scott J Medway
*Assistant Examiner* — Anh Bui
(74) *Attorney, Agent, or Firm* — McNees Wallace & Nurick LLC

(57) ABSTRACT

A dosing pump, in particular a microdosing pump, has a pump chamber in which a fluid inlet is provided at a first valve seat and a fluid outlet is provided at a second valve seat. A control element is coupled to an actuator to move the control element in order to vary the pump chamber in terms of volume. The control element is movably mounted by means of a flexure hinge.

15 Claims, 3 Drawing Sheets

DOSING PUMP

FIELD OF THE INVENTION

The invention relates to a dosing pump, in particular a so-called microdosing pump, which can be used to dispense extremely small quantities of fluid in a controlled manner.

BACKGROUND

Such microdosing pumps are employed in particular in the medical and pharmaceutical industries as well as in laboratory technology.

DE 10 2013 110 029 C5 discloses such a dosing pump. It is operated by an electrodynamic actuator with magnets for generating a magnetic field and a control element that is movable relative to the magnets. The control element includes an energizable air-core coil with a wire wound many times around a non-soft magnetic material, the air-core coil being arranged in the magnetic field and firmly coupled to a coil carrier made of a non-magnetic material. Here, the control element is mounted so as to swivel about an axis of rotation parallel to the main directions of the magnetic fields. Such a drive is also referred to as a Lorentz force actuator.

The object of the invention is to further develop a dosing pump, in particular a microdosing pump, which is distinguished by low-tolerance, repeat-accurate pumping cycles and a simple, low-wear design and setup.

SUMMARY

The invention provides a dosing pump, having a pump chamber into which a fluid inlet opens at a first valve seat and from which a fluid outlet leads out at a second valve seat, a control element, and an actuator coupled to the control element to actuate the control element, the pump chamber being varied in terms of volume by moving the control element, and the second valve seat being alternatingly closed and opened to pump fluid from the pump chamber into the fluid outlet. The control element is movably mounted by means of at least one flexure hinge.

A flexure hinge is defined as that portion of a component that has a deliberate reduction in cross-section that connects two rigid portions. The portion with the significant reduction in cross-section then permits bending and pivoting of the adjacent, rigid portions. Here, such flexure hinges have either a force-transmitting or at least a force-carrying effect and integrally connect the two portions that are movable relative to one another.

The advantage of a flexure hinge, used in a dosing pump, for the control element consists in that the position of the control element is very precisely specified, so that hardly any tolerances arise, no friction and no stick-slip effect occurs during movement, and also, there is no play in the bearing. This increases the pumping precision, in particular if a constant dosing volume is to be ensured over a long period (many pumping cycles). Furthermore, the selected design requires fewer parts than in the prior art, so that assembly is simplified as well. Owing to the flexure hinge, which is considerably easier to implement, and the omission of previous multi-part bearing designs, the dosing pump can furthermore also be of a compact configuration.

One variant of the invention provides that the control element includes a freely projecting arm hinged directly to the flexure hinge and an actuating element extending from the arm and acted upon by the actuator. This design allows a very large lever arm to be generated, i.e. the actuator is able to apply a high actuating moment through this lever arm, and in addition, a simple and precise movement of the diaphragm and a low-tolerance variation of the pump chamber are made possible by means of the large ratio of the lever arm to the pumping lift.

In particular, the arm and the actuating element are angled in relation to each other to allow a compact design and a utilization of the space in the interior of the respective housing of the dosing pump. The arm and the actuating element may also perform different functions.

For example, the arm and the actuating element may transition into each other in one piece, or they may be separate parts coupled to each other. In this case, it is possible to connect the arm and the actuating element directly to each other.

The control element may be coupled to a tappet which is adjacent to the pump chamber, the tappet being connected to the control element via a further flexure hinge. This further flexure hinge makes sure that, in spite of the pivoting movement about the first flexure hinge, the tappet has no or hardly any lateral movement components when it is moved toward and away from the pump chamber to alternately increase and decrease the volume thereof. By using two flexure hinges, a largely linear motion acts on the pump diaphragm.

No lateral sliding guide is required for the tappet. This reduces friction and in particular avoids a stick-slip effect between the moving and static components.

The actuating element may, for example, have a longitudinal axis that extends substantially parallel to the direction of movement of the tappet. The term "substantially parallel" is intended to define a deviation of no more than 15 degrees in opposite directions about the direction of movement. This configuration causes the actuating element to be deflected by the actuator preferably at right angles to its longitudinal axis. However, due to the lifting mechanism, a movement of the tappet then occurs substantially in the direction of the longitudinal axis. This means that the course of the lever is essentially L-shaped; both legs can of course take any desired shape, but the active arms of the two-armed lever meet in the first flexure hinge. The longer lever arm is usually that of the actuating element and the shorter one is that up to the tappet, resulting in a force transmission ratio.

The tappet may integrally transition, via the further flexure hinge, into a holding section which in turn is fastened to the control element, in particular so as to be non-destructively detachable. This means that the tappet is a section of a larger component which is attached to the control element by means of the holding section, in particular to the freely projecting arm here. The mounting to the arm or to the control element is usually effected by means of a fastening means, e.g. a locking pin or the like.

This configuration of the tappet allows it to be manufactured from a particularly suitable material, which may be a material different from that of the control element or the arm. This allows the fatigue strength for the further flexure hinge to be optimized.

The dosing pump is preferably a diaphragm pump, having a diaphragm that delimits and varies the pump chamber. The control element is mechanically coupled to the diaphragm, in particular by means of the above-mentioned tappet.

In particular, the tappet is moved essentially only linearly, which allows a low-fatigue movement of the diaphragm. Moreover, it is advantageous if the diaphragm is moved only perpendicular to the valve seats, which form a plane. In this way, the valve seats are opened and closed uniformly. Any leakage is thereby prevented.

The diaphragm may be clamped between an inner and an outer part, where "inner" and "outer" refer to the housing of the dosing pump, i.e. the inner part is located further inside than the outer part, which, however, does not necessarily have to define the outer shell of the housing. The outer part includes the fluid inlet and the fluid outlet, usually also the valve seats, which may however also be built-in parts fastened thereto. The inner part has a retainer for the tappet, the retainer preferably having a recess that is larger than the cross-section of the tappet so that there is a gap laterally between the tappet and the inner part in order to avoid contact. The tappet has its two ends attached to the diaphragm and to the further flexure hinge, respectively, so that it travels on a unique path of movement when the actuator is actuated.

The further flexure hinge may be located in a gap between the control element and the inner part, so that room is available here for the pivoting movement.

The control element may extend as an angled arm from the first flexure hinge around the inner part to extend between the actuator and the diaphragm. This allows the first flexure hinge to be placed in almost any position relative to the diaphragm to achieve the desired lifting movement of the diaphragm and its tappet.

According to one embodiment of the invention, the lever arm between the first flexure hinge and the effective center of the actuator is at least 3 times a lever arm between the first flexure hinge and the further flexure hinge, so that a large transmission ratio is possible with small dimensions of the dosing pump.

In particular, a plane that is defined by at least one valve seat intersects the first flexure hinge, in particular with both valve seats lying in the same plane. In this way, it is possible to allow a substantially vertical movement of the part closing the valve seat(s) during the pivoting movement defined by the first flexure hinge. In the case of a diaphragm valve with a tappet, the movement of the tappet is then substantially perpendicular to this plane.

The actuator is more particularly a Lorentz force actuator as mentioned before, the control element having an air-core coil or permanent magnets provided thereon; in particular, one of the air-core coil and the permanent magnets is/are provided at the actuating element. On the housing side, conversely, the other of the air-core coil and the permanent magnets is/are then provided.

A respective non-return valve may be positioned at each of the fluid inlet and fluid outlet, the non-return valves being adapted to be opened in the same flow direction, that is, in the pumping direction. Thus, for example, the fluid inlet may always be open during the pumping movement, so that the non-return valve controls the inflow.

Optionally, the valve seat at the fluid inlet may be closed only in specific positions, e.g. with the pump switched off.

In particular, the dosing pump includes an elastic return element, e.g. a spring that urges the control element in one direction so that it is moved in the opposite direction due to the actuator.

It has been found that the extent of the flexure hinge relative to the plane of one valve seat or both valve seats or to the neutral position of the diaphragm has different effects. The flexure hinge typically has an oblong shape in cross-section, more specifically in a sectional plane perpendicular to the plane of the valve seat(s) or the neutral position of the diaphragm, and at the same time at right angles to the pivot axis formed by the flexure hinge. The flexure hinge has an oblong shape in this cross-section and, in the longitudinal direction, may extend perpendicularly, parallel to, or obliquely to the plane of the valve seat or seats. If the longitudinal direction extends perpendicularly to this plane, the hinge is subjected primarily to a compression load, which increases long-term stability. In a parallel orientation, the bending elasticity is improved, whereas a course of the longitudinal direction that is oblique to this plane constitutes a compromise between the orientations mentioned before.

DETAILED DESCRIPTION

Figure 1:
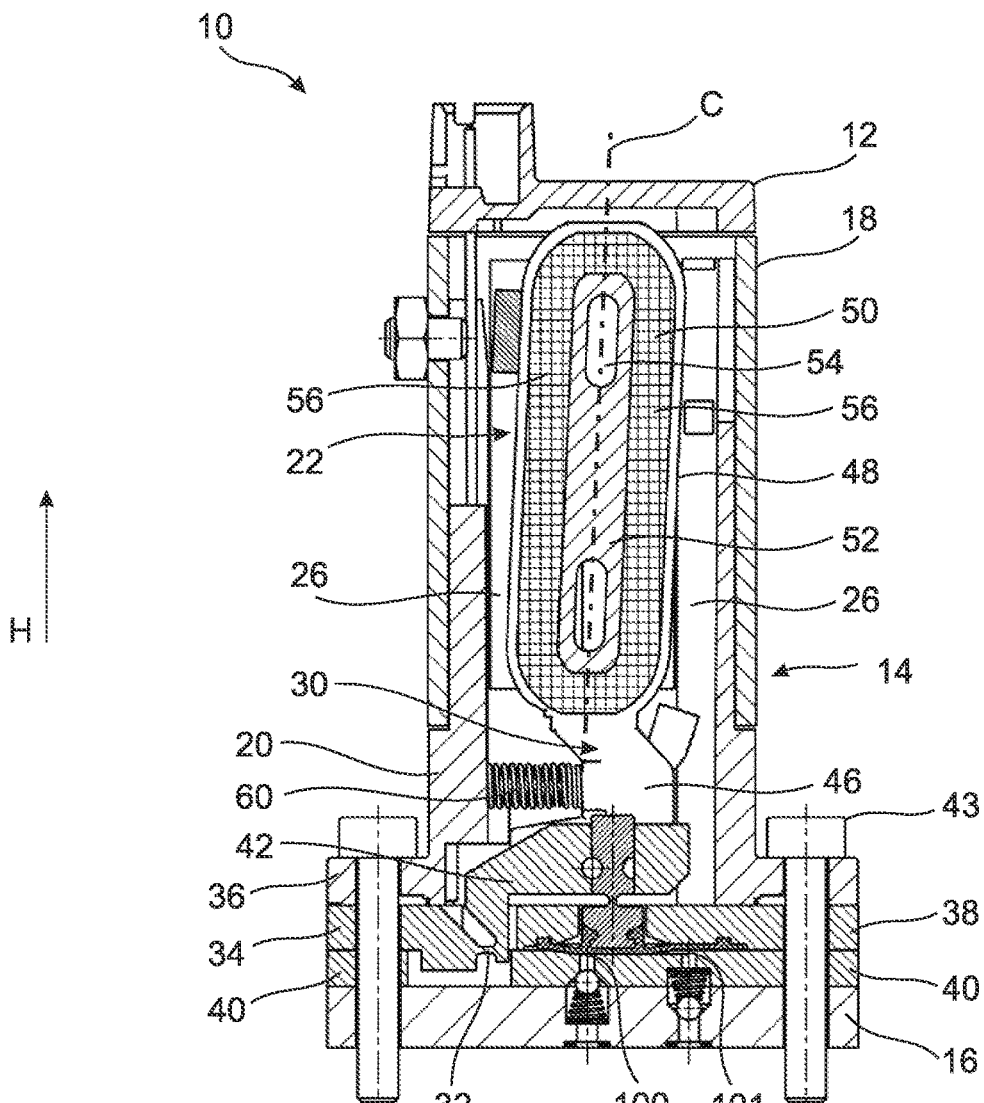
FIG. 1 shows a sectional view of an embodiment of the dosing pump according to the invention in a non-energized initial position, in which the dosing pump does not allow any fluid to flow through it.

FIG. 1 illustrates a dosing pump 10, in this case a so-called microdosing pump, which can, however, also be used as a valve.

In the following, the directional indications used refer to a proper mounting position of the dosing pump 10. Here, the dosing pump 10 is oriented along a vertical direction H.

The micropump 10 has a housing comprising an end wall 12 as part of a multi-part pot 14 and a base 16. The pot 14 constitutes a pot-shaped actuator housing and the base 16 constitutes a plate-shaped pump seat plate.

The end wall 12 is the upper end of the pot 14.

In addition to the end wall 12, the pot 14 includes a tubular, in this case cuboid, upper part 18 and a lower part 20 fitted into the upper part 18.

An actuator 22 in the form of an electromagnetic actuator, here a Lorentz force actuator, is accommodated within the housing.

The actuator 22 comprises a plurality of permanent magnets 26 which are mounted, for example, in pairs side by side to the front side, cut away above the plane of projection, of the upper part 18 and to the partially concealed rear side of the upper part 18. The permanent magnets 26 are thus arranged to be stationary in relation to the pot 14 and generate a magnetic field in which a control element 30 can move relative to the permanent magnets 26.

The control element 30 is arranged for pivoting movement within the housing, more specifically about a first flexure hinge 32.

The flexure hinge 32 is a highly thinned portion in a plate-shaped part 34, which is positioned laterally below a flange 36 of the lower part 20. On the right side in FIG. 2 and at the level of the part 34, a so-called inner part 38 is located below the flange 36 in the right half.

Located below the part 38 is a so-called outer part 40, which is also of plate-shaped design and which lies on the underside of the part 34 and the part 38 and, in turn, rests on the base 16.

In this way, the plate-shaped parts 34, 38 and 40 are clamped between the flange 36 and the base 16 by fastening means 43.

The part 34 integrally continues, via the first flexure hinge 32, into an upwardly angled arm 42, which is part of the control element 30.

Figure 2:
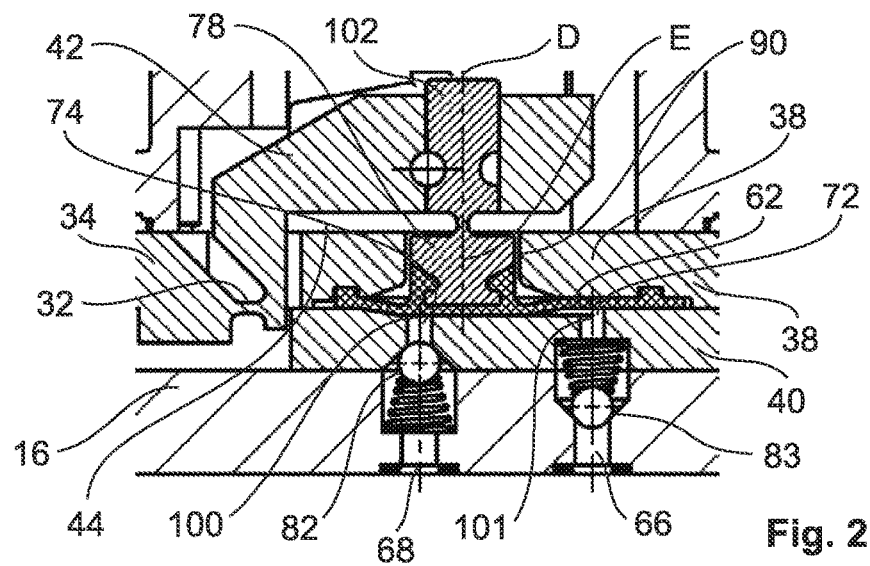
FIG. 2 shows an enlarged view of the dosing pump in the position according to FIG. 1 in the area of the pump chamber.
Figure 3:
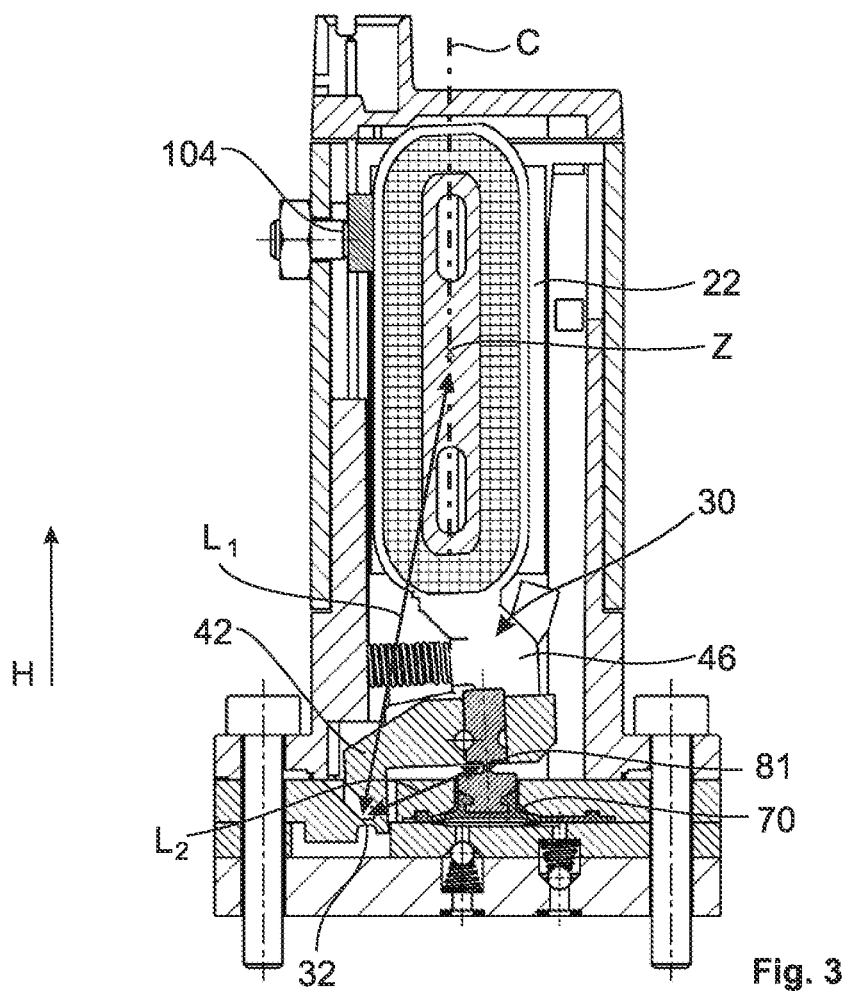
FIG. 3 shows a longitudinal sectional view of the dosing pump according to FIG. 1 shortly before fluid is ejected.

The arm 42 extends in an angled or bent manner first above the inner part 38 and then over the latter, forming a gap 44 which can be better seen in FIG. 2.

A so-called actuating element 46 extends upwards from the arm 42, the actuating element 46 either being a separate part with respect to the arm 42 and being fastened thereto, or continuing integrally into the arm 42.

In the illustrated variant, the actuating element 46 is of a two-part design with two plate-shaped parts spaced apart in the direction into the plane of projection, which receive the arm 42 between them and are coupled to it.

The actuating element 46 with the two plate-shaped parts extends upwards to the actuator and forms a so-called coil carrier 48 there.

Here, an energizable air-core coil 50 having an oval shape is attached to the coil carrier 48, enclosing a space 52, which may also include one or more cavities 54. As can be seen in FIG. 1, the space 52 may also be partly or completely filled with non-magnetic material, e.g., with a plastic material.

The energizable air-core coil 50 is thus firmly attached to the coil carrier 48 and thus to the control element 30 and is moved together with the latter.

The coil carrier 48 and thus the control element 30 are preferably made from a non-soft magnetic material, in particular from a suitable plastic material.

To shield the magnetic fields of the permanent magnets 26, the pot 14 may be formed from a suitable material as a shielding housing or, alternatively, may be made from plastic if shielding plates are received therein for shielding the magnetic fields.

The air-core coil 50 is wound with copper wire and is oval and elongated with respect to the vertical direction H.

This results in two parallel sections 56 of the air-core coil 50, through which current flows in different directions and which extend parallel to an axis of symmetry C of the air-core coil.

When the air-core coil 50 is energized, the charges moving through the windings of the air-core coil 50 generate a Lorentz force in the magnetic field of the permanent magnets 26, which causes the control element 30 to pivot about the flexure hinge 32, the pivot axis of which extends perpendicular to the plane of projection.

The air-core coil 50 is optionally energized by means of a spring-like return element 60, which, in addition to supplying current, also serves to return the overall one-armed lever constituted by the control element 30.

Now that the actuator side of the dosing pump 10 has been discussed, the fluidics side will be described below.

The dosing pump 10 shown is a diaphragm valve having a plate-shaped diaphragm 62, better visible in FIG. 2, which is clamped between the inner part 38 and the outer part 40.

Figure 4:
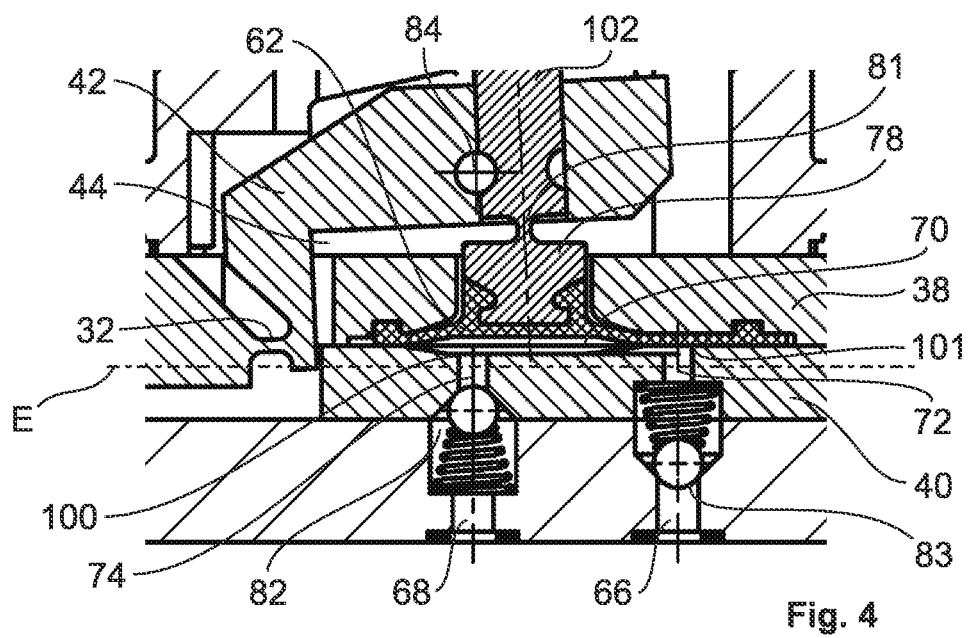
FIG. 4 shows an enlarged view of the dosing pump in the position according to FIG. 3 in the area of the pump chamber.

A fluid intake duct 66 and a fluid outflow duct 68 are provided in the base 16, which extend into the outer part 40 and there extend to a pump chamber 70 which can be better seen in FIG. 4.

The fluid intake duct 66 terminates in a fluid inlet 72, which opens into the pump chamber 70, and a fluid outlet 74 forms the starting point of the fluid outflow duct 68. A non-return valve 82, 83 is provided at each of the fluid inlet 72 and fluid outlet 74.

The fluid inlet 72 and the fluid outlet 74 each have a so-called valve seat formed thereon which, when contacted by the diaphragm 62, causes the fluid intake duct 66 or the fluid outflow duct 68 to be closed. The two valve seats (typically the annular surfaces surrounding the fluid inlet 72 and the fluid outlet 74) lie in a common plane E shown in FIG. 4.

As can also be seen in FIG. 4, the pump chamber 70 is formed in that the upper side of the outer part 40, which faces the inner part 38, is formed to be slightly concave laterally inward of the circumferential edge of the diaphragm 62, and in that the opposite lower side of the inner part 38 is also shaped to be concave.

The diaphragm 62 is firmly connected, in particular mechanically form-fittingly connected, to a tappet 78, which in turn continues via a further flexure hinge 81 into a holding section 102, which is received in the arm 42 in an appropriate opening.

The holding section 102 is firmly connected to the arm 42, for example by means of gluing or by a different form-fit.

In the illustrated embodiment, there is a locking pin 84 that extends through aligned openings in the arm 42, an annular groove in the holding section 102, and also through the two plates that form the actuating element 46, so that a plurality of parts are coupled to the locking pin 84 here.

The further flexure hinge 81 is located in the gap 44.

It can be seen well in FIG. 4 that the tappet 78 does not rest laterally against the corresponding edge of its receiving opening in the inner part 38, so that a cylindrical annular gap is formed here. In fact, the tappet 78 need not be guided laterally in the inner part 38.

FIG. 4 shows that the first flexure hinge 32 is intersected by the plane E.

In the configuration of the dosing pump according to FIGS. 1 to 4, the diaphragm 62 is never pressed against the corresponding valve seat at the fluid inlet 72, so that the fluid inlet to the pump chamber 70 is always open, although this need not necessarily be the case.

In the initial position, which is also the de-energized position shown in FIGS. 1 and 2, the return element 60 acts on the pivotal control element 30, which ensures that the arm 42 occupies a defined, lowermost pivot position, in which it can preferably be largely or completely free of stress in the region of the first flexure hinge 32.

In the initial position, the central axes D, E of the holding section 102 and the tappet 78, which can be seen in FIG. 2, are located on a common axis, i.e. this one-piece part is not bent in the region of the second flexure hinge 81. The longitudinal axis C extends at a slight angle to the axes D, E and to the vertical direction H. In this position, the diaphragm 62 presses against the valve seat at the fluid outlet 74. While fluid can flow into a part of the pump chamber 70 via the non-return valve 83, which is open in this case, and the fluid inlet 72, it cannot flow out.

When energized, the Lorentz force actuator acts to cause the air-core coil 50, as seen in FIG. 2, to pivot to the left at its upper end, which in turn means that the arm 42 pivots upward in a counterclockwise direction and, in doing so, entrains the holding section 102 and, via the second flexure hinge 81, also the tappet 78, which in turn causes the diaphragm 62 to be lifted. The valve seat at the fluid outlet 74 is then open, so that fluid is sucked in by the lifting action, and the non-return valve 83 is also necessarily open, whereas the non-return valve 82 is closed so as to prevent previously pumped-out fluid from being sucked back from the fluid outlet 74.

After the tappet 78 has reached its top dead center, which is shown in FIG. 4, the current can be switched off again or the polarity of the actuator can be reversed. In either case, a backward movement occurs, which results in the arm 42 pivoting downward and the tappet 78 also pressing the diaphragm 62 downward. The pump chamber 70 is reduced in volume, with the outflow of the fluid taking place exclusively via the fluid outlet 74 and the non-return valve 82 which is pressed open in the process, whereas the non-return valve 83 effectively prevents outflow via the fluid inlet 72.

In the top dead center position, the longitudinal axis C is oriented in the vertical direction H, whereas the axes D and E are tilted in relation to each other so that a small bend exists in the further flexure hinge 81.

The top dead center may be limited by an adjustable stop 104 to set a defined pumping lift (a defined pumping volume).

Figure 5:
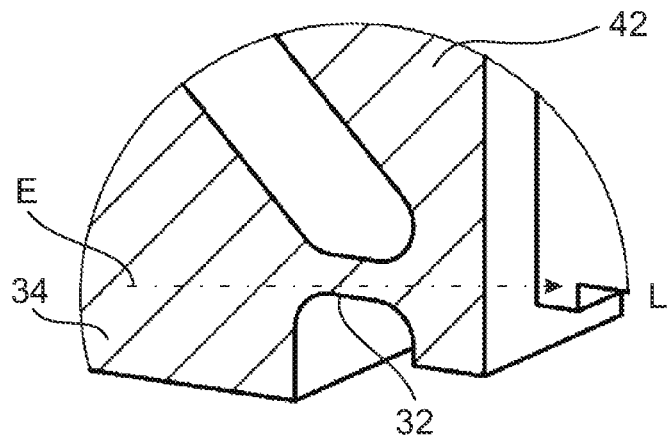
FIG. 5 shows an enlarged sectional view of the first flexure hinge according to a first variant.
Figure 6:
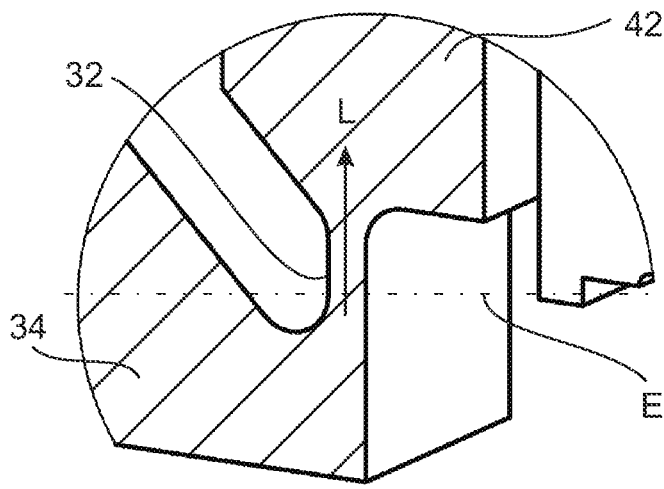
FIG. 6 shows a perspective sectional view of a further embodiment of the first flexure hinge.
Figure 7:
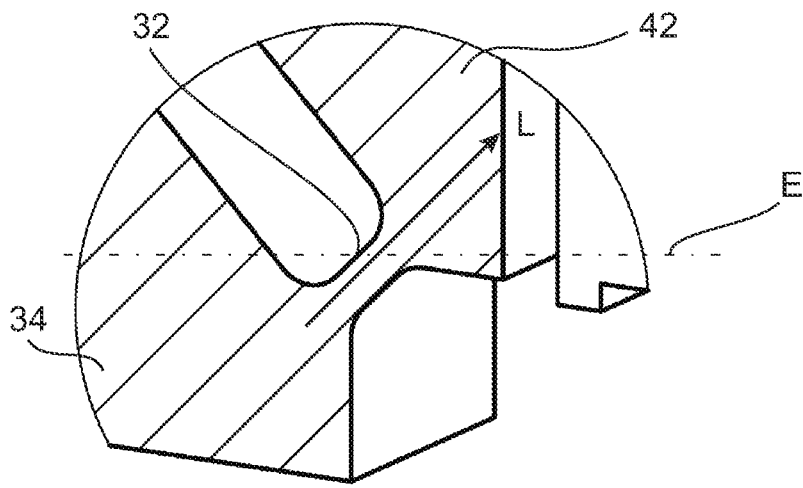
FIG. 7 shows a perspective sectional view of yet another embodiment of a first flexure hinge.

The first flexure hinge 34 has an oblong shape having a longitudinal direction L in cross-section (see FIG. 5) perpendicular to the plane E, here parallel to the plane of projection. In the embodiment according to FIGS. 1 to 4, this longitudinal direction L runs parallel to the plane E in the non-loaded state of the dosing pump. In the variant according to FIG. 6, the longitudinal direction L extends perpendicular to the plane E, and in the embodiment according to FIG. 7, it extends obliquely thereto, preferably in the range of about 45 degrees. Each orientation has advantages in terms of flexibility of the arm 42 and durability of the flexure hinge 32.

As is apparent from the drawings, the actuator 22 produces a movement of the control element 30 at its upper end in the horizontal direction, i.e., parallel to the plane E, this being only one exemplary embodiment. However, the movement of the tappet 78 occurs substantially perpendicular to the plane E, that is, substantially at an angle of 90 degrees to the movement of the actuator 22.

A further advantage of the dosing pump illustrated consists in that the lever arm of the actuator 22 is substantially larger than that of the arm 42 actuated by it for moving the tappet 78, so that the pump is able to dose very precisely, since the travel of the actuator 22 is large in comparison with the stroke movement of the tappet 78. Thus, the lever arm $L_1$ between the first flexure hinge 32 and the effective center Z of the actuator 22 (center of the area of the space circumscribed by the coil) is larger than the lever arm L2 between the first flexure hinge 32 and the second flexure hinge 81 by at least a factor of 3 (see FIG. 3).

It should be appreciated that while in the illustrated embodiment the actuator 22 is a Lorentz force actuator, the invention is not limited to such an actuator. Rather, other actuators, electromagnetic actuators or other types of actuators, may also be used.

The features and variants illustrated can be combined with each other as desired; also, while these variants and embodiments are advantageous, the individual features need not necessarily be realized exactly as depicted in the Figures.

The invention claimed is:

1. A dosing pump, comprising a pump chamber into which a fluid inlet opens at a first valve seat and from which a fluid outlet leads out at a second valve seat, a control element, and an actuator coupled to the control element to move the control element, the pump chamber being varied in terms of volume by moving the control element, and the second valve seat being alternatingly closed and opened to pump fluid from the pump chamber into the fluid outlet, and wherein the control element is movably mounted by at least a first flexure hinge, the first flexure hinge being positioned between a first plate-shaped part and an arm, the first flexure hinge being a thin portion having a reduced cross-section with respect to the first plate-shaped part for permitting pivoting of the arm with respect to the first plate-shaped part, the arm having an upwardly angled arm portion relative to the first flexure hinge, wherein the first plate-shaped part is integrally formed, via the first flexure hinge, with the upwardly angled arm portion.

2. The dosing pump according to claim 1, wherein the control element includes a freely projecting arm hinged directly to the first flexure hinge and an actuating element extending from the arm and acted upon by the actuator.

3. A dosing pump, comprising a pump chamber into which a fluid inlet opens at a first valve seat and from which a fluid outlet leads out at a second valve seat, a control element, and an actuator coupled to the control element to move the control element, the pump chamber being varied in terms of volume by moving the control element, and the second valve seat being alternatingly closed and opened to pump fluid from the pump chamber into the fluid outlet, and wherein the control element is movably mounted by at least a first flexure hinge, the first flexure hinge being a portion of a component that has a deliberate reduction in cross-section that connects a rigid portion and an arm, wherein the control element includes the arm hinged directly to the first flexure hinge and an actuating element extending from the arm and acted upon by the actuator, the arm includes an upwardly angled arm portion relative to the first flexure hinge, wherein the arm and the actuating element transition into each other in one piece, and wherein the first flexure hinge permits pivoting the arm with respect to the rigid portion.

4. The dosing pump according to claim 1, wherein the holding section is fastened to the control element so as to be non-destructively detachable.

5. The dosing pump according to claim 1, wherein a lever arm between the first flexure hinge and an effective center of the actuator corresponds to at least 3 times a lever arm between the first flexure hinge and a second flexure hinge.

6. A dosing pump, comprising a pump chamber into which a fluid inlet opens at a first valve seat and from which a fluid outlet leads out at a second valve seat, a control element, and an actuator coupled to the control element to move the control element, the pump chamber being varied in terms of volume by moving the control element, and the second valve seat being alternatingly closed and opened to pump fluid from the pump chamber into the fluid outlet, and wherein the control element is movably mounted by at least a first flexure hinge, the first flexure hinge being a portion of a component that has a deliberate reduction in cross-section that connects a rigid portion and an arm, wherein the control element includes the arm hinged directly to the first flexure hinge and an actuating element extending from the arm and acted upon by the actuator, the arm includes an upwardly angled arm portion relative to the first flexure hinge, wherein the flexure hinge permits pivoting of the arm with respect to the rigid portion, wherein the dosing pump is a diaphragm pump, and a diaphragm delimits and varies the pump chamber, the control element being mechanically coupled to the diaphragm, the diaphragm being lifted and downed by one single part only which is a tappet attached to the control element, the control element being connected to the membrane by the tappet, only.

7. The dosing pump according to claim 6, wherein the control element is mechanically coupled to the diaphragm by a tappet.

8. The dosing pump according to claim 1, wherein the dosing pump is a diaphragm pump, and a diaphragm delimits and varies the pump chamber, the control element being mechanically coupled to the diaphragm and wherein the diaphragm is clamped between inner and outer parts, of which the outer part includes the fluid inlet and the fluid outlet and the inner part has a retainer for the tappet.

9. The dosing pump according to claim 8, further comprising a second flexure hinge, wherein the second flexure hinge is located in a gap between the control element and the inner part.

10. The dosing pump according to claim 8, wherein the control element extends as an angled arm from the first flexure hinge around the inner part to extend between the actuator and the diaphragm.

11. The dosing pump according to claim 1, wherein the first flexure hinge is intersected by a plane that is defined by a neutral position of the diaphragm or at least one valve seat.

12. The dosing pump according to claim 1, wherein the actuator is a Lorentz force actuator, and an air-core coil or permanent magnets are provided at the control element.

13. The dosing pump according to claim 1, wherein a respective non-return valve is positioned at each of the fluid inlet and the fluid outlet.

14. The dosing pump according to claim 1, wherein the first flexure hinge has an oblong shape in cross-section and, in its longitudinal direction, extends perpendicularly, parallel or obliquely to a plane that is defined by a neutral position of the diaphragm or at least one valve seat.

15. The dosing pump according to claim 1, wherein the control element is coupled to a tappet which is adjacent to the pump chamber and connected to the control element via a second flexure hinge, wherein the tappet integrally transitions, via the second flexure hinge, into a holding section which in turn is fastened to the control element.

\* \* \* \* \*